United States Patent [19]

Kelman

[11] Patent Number: 4,495,665
[45] Date of Patent: Jan. 29, 1985

[54] POSTERIOR CHAMBER INTRAOCULAR LENS AND METHOD OF MAKING AN OPENING IN A CAPSULE

[76] Inventor: Charles D. Kelman, 269 Grand Central Pkwy., Floral Pk., N.Y. 11005

[21] Appl. No.: 455,537

[22] Filed: Jan. 4, 1983

[51] Int. Cl.³ .............................. A61F 1/16; A61F 1/24
[52] U.S. Cl. .......................................................... 3/13
[58] Field of Search ............................................ 3/13, 1

[56] References Cited

U.S. PATENT DOCUMENTS 4,244,060  1/1981  Hoffer ........................................ 3/13
4,412,359  11/1983 Myers ........................................ 3/13

OTHER PUBLICATIONS

Model PC-11, Posterior Chamber (Advertisement), manufactured by American Medical Optics, American Hospital Supply Corp., 1402 East Alton Ave., Irvine, Calif., Aug. 1981.

Primary Examiner—Ronald L. Frinks
Attorney, Agent, or Firm—Henry Sternberg

[57] ABSTRACT

A posterior chamber intraocular lens having at least two projections on the rear surface thereof for causing a line of tension in the posterior capsule. If desired, after implantation of the lens the posterior capsule may be perforated with a laser beam transversely to the line of tension, causing the posterior capsule to tear and form an opening to eliminate any cloudiness of the posterior capsule from behind the central region of the lens.

10 Claims, 3 Drawing Figures

POSTERIOR CHAMBER INTRAOCULAR LENS AND METHOD OF MAKING AN OPENING IN A CAPSULE

This invention relates to posterior chamber intraocular lenses and to a method of making an opening in the capsule of an eye, and more particularly, in the posterior capsule of a human eye. As used herein, posterior chamber lenses include lenses of the type having a lens body or optic positioned in the capsule of the eye although one or more position-fixation members therefor may be seated outside the capsule or outside the posterior chamber, for example, in the anterior chamber.

After an intraocular lens has been implanted in an eye following the removal of a natural lens having, for example, a cataract condition, by extracapsular surgery, the posterior capsule which remains in the eye may at some later time become clouded and require an opening to be made therein for clear vision. A laser beam may be used to make successive perforations in the posterior capsule, which perforations join together to form the desired opening.

To the best of my knowledge, such laser surgery in the past has required the perforations to be made along substantial portions of the periphery of the desired opening, thus requiring many laser perforations and a correspondingly lengthy operating procedure.

I propose that a laser beam can be used to make a desired opening in the posterior capsule with fewer perforations than were heretofore made. I also propose that a lens constructed in accordance with my invention facilitates making an opening in the posterior capsule more quickly and with fewer laser beam perforations of the posterior capsule than were heretofore made.

In accordance with the invention, a posterior chamber intraocular lens comprises a lens body including a rear surface having thereon at least two projections having a total length along the rear surface in a direction transverse to the distance between said projections which is small relative to said distance between said projections. The lens also includes position-fixation means extending from the lens body for positioning the lens body in the capsule of an eye and for pressing the projections against the posterior capsule. The projections are effective to cause tension of the posterior capsule in the region between at least two of the projections, sufficient to tear the posterior capsule after perforation of the capsule in said region between at least two of said projections.

Figure 1:
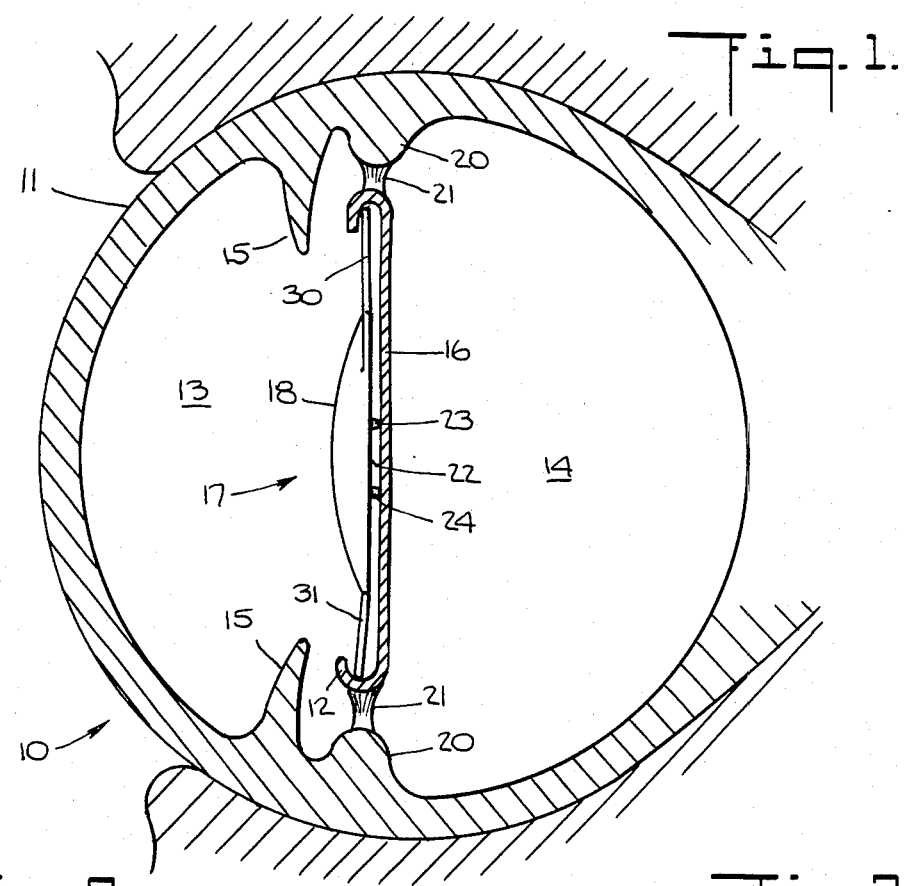
FIG. 1 is a fragmentary sectional view illustrating a first preferred embodiment of the lens of the present invention within the posterior chamber capsule.

Referring now more particularly to FIG. 1 of the drawings, a human eye 10 is represented in section, with portions omitted for the sake of clarity. The eye 10 includes a cornea 11. Anterior chamber 13 and posterior chamber 14 are defined by the position of the iris 15. A membrane or posterior capsule 16 supports a lens 17 constructed in accordance with the invention and implanted by the surgeon after the anterior capsule (only a small portion 12 of which remains) and natural lens (not shown) which may have had a cataract therein were removed surgically. The capsule 16 is normally connected to the ciliary body 20 by a plurality of zonules 21.

Figure 2:
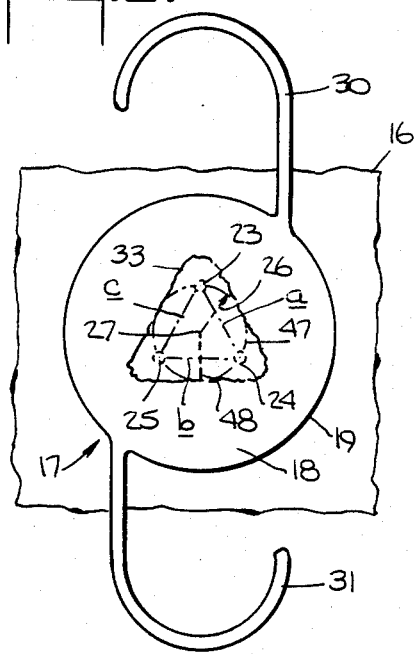
FIG. 2 is an elevational view of the lens in accordance with the FIG. 1 embodiment of the present invention within the posterior capsule.

The lens 17 includes a lens body 18 having a rear surface 22 having thereon at least two spaced projections and preferably three spaced projections 23, 24, 25, represented in FIGS. 1 and 2. The lens body 18 preferably has a substantially circular periphery 19 and a substantially circular middle portion having an imaginary periphery 47 defined by a radius 26 from the optical axis 27 equal to about one sixth the diameter of the lens body 18. The projections 23, 24, 25 are preferably positioned along said imaginary periphery 47 at the rear surface 22.

The projections 23, 24, 25 have a total length in a direction transverse to the distances a, b, c between the projections which is small relative to the distances a, b, or c and preferably is one-half or less relative to the distances a, b or c. The projections 23, 24, 25 preferably individually are projections substantially at individual points of the rear surface 22 of the lens body, each projection preferably having a maximum dimension along said rear surface not greater than 1 millimeter and each projection is shaped so as to make substantially single point contact with the posterior capsule 16. Preferably the length of each of the projections 23, 24, 25 in a direction extending from the rear surface of the lens body is in the range of from 0.25 millimeter to 1 millimeter.

The lens of FIGS. 1 and 2 includes position-fixation means comprising two members extending from the lens body 18 for positioning the lens body in the capsule of an eye and for pressing the projections 23, 24, 25 against the posterior capsule 16. The projections 23, 24, 25 are effective to cause a substantially concentrated line of tension of the posterior capsule in the region between at least two of the projections sufficient to tear the posterior capsule after laser perforation of the capsule in said region. Such tear is, as a result of the tension line, substantially greater in size than would otherwise be expected to result from the laser perforation only. In other words, fewer laser perforations are required to accomplish the same size opening in the posterior capsule.

The position fixation members 30, 31 may be of conventional construction but preferably are at a slight forward angle with respect to the plane of the rear surface 22 of the lens body 17 to augment the pressing of the projections 23, 24, 25 against the posterior capsule 16.

Figure 3:
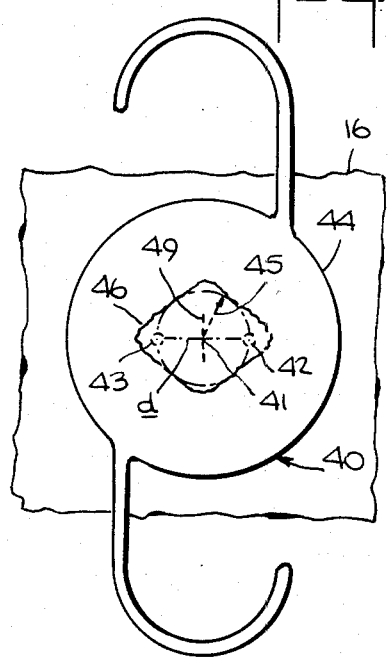
FIG. 3 is an elevational view of another embodiment of the present invention within the posterior capsule.

Referring now more particularly to FIG. 3 of the drawings, there is represented a lens 40 similar to the lens 17 and having an optical axis 41. The lens 40 includes two projections 42, 43 similar to the projections 23, 24, 25 of the lens 17 and spaced at substantially equal distances from the optical axis 41. The projections 42, 43 may, for example, be spaced from each other by a distance d of at approximately two millimeters and preferably are located on the periphery of the middle portion of the rear surface of the lens body 44 defined by a radius 45 from the optical axis 41 equal to about one sixth the diameter of the lens body 44.

In both FIGS. 2 and 3 a fragmentary portion of the posterior capsule 16 is represented behind the lens.

Referring again to FIGS. 1 and 2, after the lens 17 is seated, lines of tension exist in the posterior capsule 16 between the pairs of projections 23, 24 and 24, 25 and 23, 25, generally corresponding to the broken-lines representing distances a, b and c of the lens. If it is desired at some time after implantation of the lens to open the central region of the posterior capsule, the surgeon may perforate the posterior capsule 16 with a laser beam in one or more directions transverse to one or more of the lines of tension, with perforations crossing one or more of the lines of tension, causing the posterior capsule to tear to form an opening 33 in the posterior capsule 16. An imaginary line along which laser perforations may, for example, be made is represented by broken line 48.

Referring to FIG. 3, the surgeon may perforate the posterior capsule 16 with a laser beam in a direction transverse to the line of tension generally corresponding to the broken line representing the distance d with perforations crossing the line of tension, causing the posterior capsule to tear to form an opening 46 in the membrane 16. An imaginary line along which laser perforations may, for example, be made is represented by broken line 49.

While there have been described what are at present cosidered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. A posterior chamber intraocular lens comprising:
   a lens body including a rear surface having thereon at least two projections together having a total length along said rear surface in a direction transverse to the distance between said projections which is small relative to said distance between said projections; and
   position-fixation means extending from said lens body for positioning said lens body in the capsule of an eye and for pressing said projections against the posterior capsule, each of said projections shaped so as to make substantially single point contact with said posterior capsule and said projections being effective to cause tension of the posterior capsule in said region between at least two of said projections sufficient to tear the posterior capsule after perforation of the capsule in said region between at least two of said projections.

2. A lens in accordance with claim 1 which has an optical axis, said lens body having a substantially circular periphery and said projections being on the periphery of the middle portion of the rear surface of said lens body defined by a radius from said optical axis equal to about one sixth of the diameter of said lens body.

3. A lens in accordance with claim 1 in which said distance between said projections is at least twice as long as the total length of said projections in a direction transverse to the line along which the distance between said projections is measured.

4. A lens in accordance with claim 1 in which said projections individually are projections substantially at individual points of said rear surface of said lens body, each having a maximum dimension along said rear surface not greater than about 1 millimeter.

5. A lens in accordance with claim 1 in which the length of each of said projections in a direction extending from said rear surface of said lens body is in the range of from 0.25 millimeter to 1 millimeter.

6. A lens in accordance with claim 1 which has an optical axis and which includes three of said projections positioned substantially at the vertices of an imaginary equilateral triangle and at substantially equal distances from said optical axis.

7. A lens in accordance with claim 1 which has an optical axis and which includes two of said projections spaced at substantially equal distances from said optical axis.

8. A lens in accordance with claim 1 which includes two of said projections spaced from each other by a distance of approximately 2 millimeters.

9. A method of making an opening in the posterior capsule of an eye comprising:
   inserting into the capsule of an eye an intraocular lens having spaced projecting portions on the rear surface of the lens body, said projecting portions together having a total length along said rear surface in a direction transverse to the distance between said projecting portions which is small relative to the distance between said projecting portions, each of said projecting portions shaped so as to make substantially single point contact with said posterior capsule thereby causing said projecting portions to press against the posterior capsule for forming at least one line of tension in the posterior capsule in the region between said projecting portions; and
   perforating the posterior capsule with a laser beam in a direction transverse to the line of tension of the posterior capsule, whereby the posterior capsule tears to form an opening.

10. A method in accordance with claim 9 in which the step of perforating the posterior capsule with a laser beam includes making perforations crossing the line of tension.

* * * * *